United States Patent
Gillman et al.

(10) Patent No.: US 9,414,846 B2
(45) Date of Patent: Aug. 16, 2016

(54) DEVICES AND METHODS FOR KNEE REPLACEMENT

(71) Applicants: Michael Gillman, Laguna Beach, CA (US); Benjamin A. Gillman, Laguna Beach, CA (US)

(72) Inventors: Michael Gillman, Laguna Beach, CA (US); Benjamin A. Gillman, Laguna Beach, CA (US)

(73) Assignee: Bullseye Hip Replacement, LLC, Las Vegas, NV (US)

( * ) Notice: Subject to any disclaimer, the term of this patent is extended or adjusted under 35 U.S.C. 154(b) by 0 days.

(21) Appl. No.: 14/521,031

(22) Filed: Oct. 22, 2014

(65) Prior Publication Data

US 2016/0113661 A1 Apr. 28, 2016

(51) Int. Cl.
| | |
|---|---|
| A61B 17/15 | (2006.01) |
| A61B 17/17 | (2006.01) |
| G05B 19/4097 | (2006.01) |
| A61B 17/56 | (2006.01) |
| A61B 17/00 | (2006.01) |

(52) U.S. Cl.
CPC .............. *A61B 17/154* (2013.01); *A61B 17/155* (2013.01); *A61B 17/157* (2013.01); *A61B 17/158* (2013.01); *A61B 17/1764* (2013.01); *G05B 19/4097* (2013.01); *A61B 17/1767* (2013.01); *A61B 2017/00526* (2013.01); *A61B 2017/568* (2013.01); *G05B 2219/35012* (2013.01)

(58) Field of Classification Search
CPC ........... A61B 17/155; A61B 2019/508; A61B 2017/568
USPC .......................................................... 623/20.14
See application file for complete search history.

(56) References Cited

U.S. PATENT DOCUMENTS

| | | | | |
|---|---|---|---|---|
| 8,337,501 | B2 * | 12/2012 | Fitz et al. | 606/86 R |
| 8,617,170 | B2 | 12/2013 | Ashby et al. | |
| 8,617,171 | B2 | 12/2013 | Park et al. | |
| 8,777,875 | B2 | 7/2014 | Park | |
| 2007/0226986 | A1 * | 10/2007 | Park et al. | 29/592 |
| 2009/0088760 | A1 * | 4/2009 | Aram et al. | 606/87 |
| 2009/0131941 | A1 * | 5/2009 | Park et al. | 606/87 |
| 2010/0087829 | A1 * | 4/2010 | Metzger et al. | 606/96 |
| 2011/0106093 | A1 * | 5/2011 | Romano et al. | 606/88 |
| 2011/0245835 | A1 * | 10/2011 | Dodds et al. | 606/87 |
| 2012/0123423 | A1 * | 5/2012 | Fryman | A61B 17/15 606/89 |
| 2012/0130434 | A1 | 5/2012 | Stemniski | |
| 2012/0265496 | A1 | 10/2012 | Mahfouz | |
| 2012/0296339 | A1 | 11/2012 | Iannotti et al. | |
| 2013/0123789 | A1 | 5/2013 | Park | |
| 2013/0184764 | A1 | 7/2013 | Stone et al. | |
| 2013/0190768 | A1 | 7/2013 | Aram et al. | |
| 2013/0317510 | A1 | 11/2013 | Couture et al. | |

(Continued)

FOREIGN PATENT DOCUMENTS

WO 2013/188960 A1 12/2013

*Primary Examiner* — David Bates
(74) *Attorney, Agent, or Firm* — Seed IP Law Group PLLC

(57) ABSTRACT

A device for use in joint replacement surgery is disclosed, the device may comprise a patient-specific jig having a body formed using three dimensional data corresponding to a first resection surface of a bone of a patient according to a preoperative plan. The body may also include a first bone facing surface configured to match the first resection surface of the bone of the patient according to the three dimensional data and an alignment perimeter sized and shaped to match a perimeter of the resection surface of the bone of the patient according to the three dimensional data.

15 Claims, 9 Drawing Sheets

(56) References Cited

U.S. PATENT DOCUMENTS

| | | |
|---|---|---|
| 2014/0025348 A1 | 1/2014 | Abiven |
| 2014/0066937 A1* | 3/2014 | Wiebe, III .............. A61B 17/70 606/88 |
| 2014/0074100 A1* | 3/2014 | Murray et al. .................. 606/88 |
| 2014/0114319 A1* | 4/2014 | Wilkinson ...................... 606/88 |
| 2014/0114320 A1* | 4/2014 | Kurtz .............................. 606/88 |
| 2014/0128875 A1 | 5/2014 | Park et al. |
| 2014/0128876 A1 | 5/2014 | Aram et al. |
| 2014/0142580 A1 | 5/2014 | Aram et al. |
| 2014/0163564 A1* | 6/2014 | Bollinger ........... A61B 17/1666 606/91 |
| 2014/0188119 A1* | 7/2014 | Catanzarite et al. ............ 606/88 |
| 2014/0257309 A1 | 9/2014 | Aram et al. |

\* cited by examiner

DEVICES AND METHODS FOR KNEE REPLACEMENT

BACKGROUND

1. Technical Field

The present disclosure relates to devices and methods for the replacement of joints, and more particularly, to patient-specific knee replacement devices, including methods of manufacturing and using such devices for achieving accurate resection of patient bones and accurate placement of prosthetics based on computer generated imaging of a patient.

2. Background of the Invention

One known method of treating knee and other joints with arthritis and other medical conditions is to replace surfaces of articulating joints with prosthetic devices through surgical procedures. It is critical that such prosthetic devices are accurately designed and manufactured and that they are installed correctly so that they relieve pain and provide an effective treatment method for such ailments. An orthopedic surgeon performing such joint replacement on a patient seeks to ensure, through surgery, adequate placement of the prosthetic and proper reconstruction of the joint being replaced. A particular patient's bone structure symmetry is one important consideration that a surgeon must consider when performing joint replacement surgery. Additionally, malposition of joint replacement prosthetics can result in untoward pain or premature wear of the bearing surfaces, which may require additional surgeries to correct. Improperly sized prosthetic components that are tool large or too small may also cause pain, loosening of prostheses or accelerated wear. Repairing improperly sized prosthetic components may require additional surgeries.

In the case of a knee, the condition of the patient's joint may require a partial or total replacement. A partial knee replacement may involve removing the joint surfaces of one or more of the femur, tibia, or patella bones in the medial, lateral, or patellofemoral compartments. A partial knee replacement may include replacing one or more surfaces of the upper tibia, the shin bone, and the lower femur, including the articular surface, the medial condyle, or the lateral condyle. A partial knee replacement may also include removing and replacing the inner or underside surface of the patella, also called the knee cap. A total knee replacement typically involves removal and replacement of the lower surface or distal portion of the femur, including the medial and lateral condyles; replacement of the upper surface or proximal portion of the tibia, including the medial and lateral condyles; and replacement of the inner or underside surface of the patella.

In total knee replacement, the removed bone and anatomy is typically replaced with a prosthesis. The removed parts of the femur are replaced with a femoral component, the removed parts of the tibia are replaced with a tibial component, and the surface of the patella is replaced with a patellar component. A polymer spacer is usually placed between the femoral and tibial components as an articulating surface to facilitate smooth movement between the surfaces of the components.

One concern during the bone removal stage of a knee replacement surgery is that the surgeon may not make the correct cuts to the bones which may result in malaligned prosthesis and a poorly functioning knee replacement. Therefore, accurate removal and resurfacing of the knee bones is an important part of a knee replacement surgery. Surgeons may use cutting guides and cutting blocks to assist in the cutting or sectioning of the knee bones.

Another concern is that a surgeon may place a final prosthetic that is either too small or too large for a patient's bone. Both improper bone cuts and improper sized implants may lead to untoward pain, early wear, or early loosening of prostheses that may result in a secondary unnecessary surgery.

With the assistance of computer generated data derived from CT, MRI, or other scans, such as X-rays, surgeons can more effectively determine proper alignment and positioning of the knee prosthetics in a patient through 3D modeling and rendering. Some surgeons use guides or generic extramedullary or intramedullary cutting guides during surgery in an attempt to properly place the prosthetics; however, accuracy and simplicity of existing devices and methods remain limited due to a variety of factors.

BRIEF SUMMARY

A device for use in joint replacement surgery is disclosed, the device may comprise a patient-specific jig having a body formed using three dimensional data corresponding to a first resection surface of a bone of a patient according to a preoperative plan. The body may also include a first bone facing surface configured to match the first resection surface of the bone of the patient according to the three dimensional data and an alignment perimeter sized and shaped to match a perimeter of the resection surface of the bone of the patient according to the three dimensional data.

A method for use in joint replacement surgery is disclosed. The method may include generating a bone surface image from three dimensional image data from the bone structure of a patient. The method may also include generating a bone resection image based on a final installation position of a prosthesis and the three dimensional image data from the bone structure of a patient and generating a patient specific resection jig image superimposed proximate the bone resection image. Machine control data from the patient specific resection jig image may also be generated.

DETAILED DESCRIPTION

Figure 1:
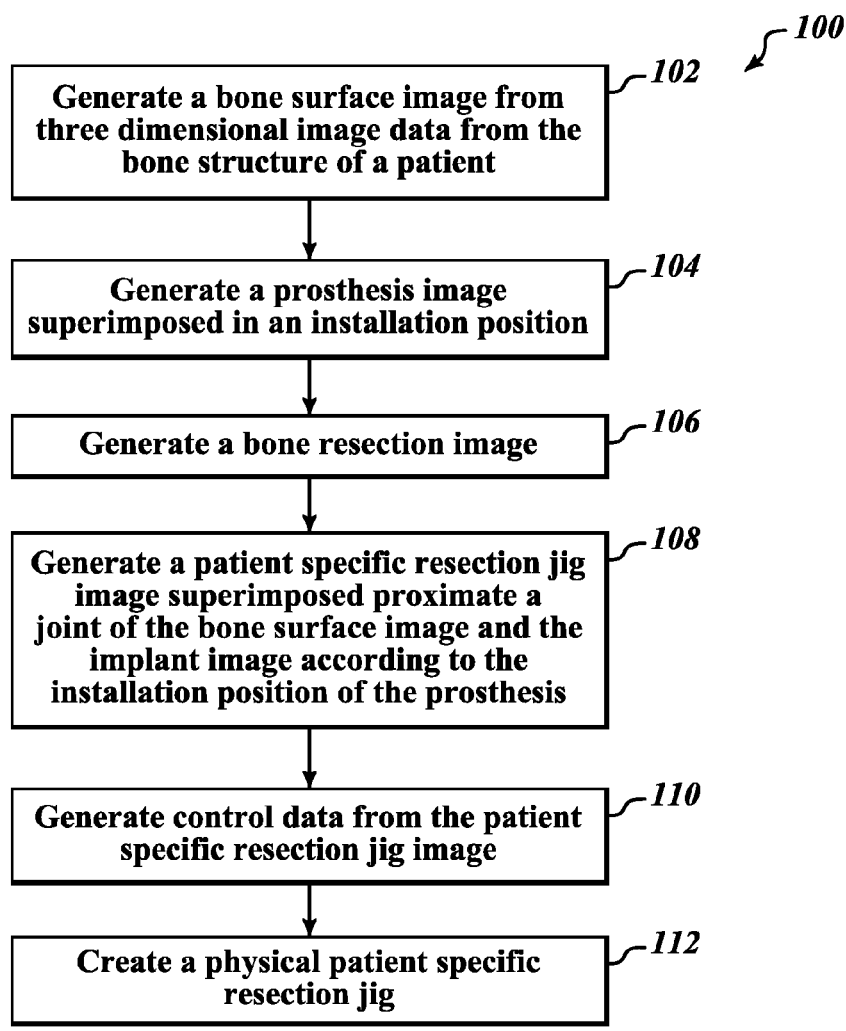
FIG. 1 depicts a method according to one or more embodiments disclosed herein.

The present disclosure pertains to patient-specific knee replacement devices and methods of designing, manufacturing, and using such devices for achieving accurate component or prosthesis sizing and placement during knee replacement surgery based on computer generated imaging of a particular patient. When an orthopedic surgeon recommends knee replacement surgery for a particular patient, a variety of images may be obtained utilizing CT, MRI, and other scans, such as x-rays, to generate 3D modeling of the patient's bone structure, particularly the femur, the tibia, and then patella. From such 3D models, the surgeon may determine the specific, final size, geometry, location, and orientation of the femoral component, tibial component, and patellar components to be secured to the patient's bones during surgery. Surgeons may select the prosthetics from a number of standard sizes and shapes or may use patient-specific prosthetics.

Once the final size, geometry, location, and orientation of the prosthetics are determined, the surgeon may create one or more patient-specific jigs to be installed on the patient's knee bones during the surgery to confirm accurate removal and preparation of the patient's bones. The patient-specific jigs may also include features such as guide holes or apertures for guiding additional bone preparation procedures. These patient-specific jigs may conform to the shape of a properly prepared bone such that, during surgery, if the jig does not properly engage with the prepared bone structure of the patient, the surgeon knows that additional primary bone preparation may be necessary to prepare the bones for accurate placement of the prosthetics in the patient.

A femoral patient-specific jig may be designed and manufactured based on a patient-specific distal femur end. The patient-specific jig can be developed as either physical components via a prototyping machine or visual representations in a 3D modeling software program based upon the 3D images of the patient.

The methods and systems disclosed herein are based at least in part on pre-operating (pre-operative) imaging and at least in part on orthopedic surgical procedures based upon the pre-operative methods and systems. As is understood in the art, pre-operative imaging has a number of different purposes and generally is performed to help guide the surgeon during the surgical procedure, allow for patient-specific tools, or implants to be formed, and etc. The present disclosure may be part of a system for designing and constructing one or more patient-specific jigs for use in an orthopedic surgical procedure in which knee replacement components are prepared, orientated, and implanted. The referenced systems and methods are now described with reference to the accompanying drawings, in which one or more illustrated embodiments or arrangements of the systems and methods are shown in accordance to one or more embodiments disclosed herein. Aspects of the present systems and methods can take the form of an entirely hardware embodiment, an entirely software embodiment (including firmware, resident software, micro-code, etc.), or an embodiment combining software and hardware. One of skill in the art can appreciate that a software process can be transformed into an equivalent hardware structure, and a hardware structure can itself be transformed into an equivalent software process. Thus, the selection of a hardware implementation versus a software implementation is one of design choice and left to the implementer.

Figure 2:
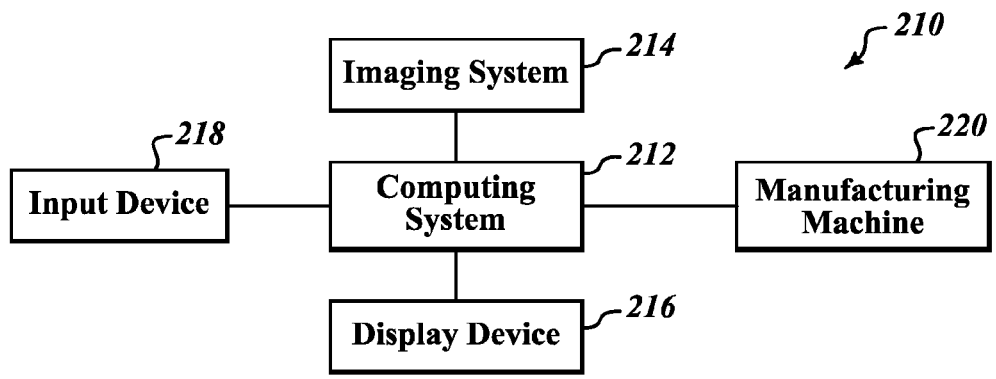
FIG. 2 depicts a system according to one or more embodiments disclosed herein.

FIG. 1 is a flow diagram illustrating a method pertaining to pre-operative imaging and planning according to aspects of the present disclosure. FIG. 2 shows a system for carrying out the methods of the present disclosure, such as that described with reference to FIG. 1. FIG. 2 shows a simplified system 210 of devices that may be used to carry out the methods of the present disclosure. The system 210 comprises a computing system 212 coupled to an imaging system 214. The imaging system 214 captures patient image data and transfers the data to the computing system 212. The computing system 212 processes such data and transmits the data to a display device 216 for display of images and other data. An input device 218 receives input from a computer or an operator (such as a surgeon) and transmits inputted information to the computing system 212 for processing. Such input devices 218 are well known in the art and will not be described in greater detail. The imaging system 214 may include a bone imaging machine for forming three-dimensional image data from a bone structure of a patient. The computing system 212 may include a patient-specific device generator for processing and generating images, and a patient-specific device converter for generating design control data. A manufacturing machine 220 receives the control data from the computing system 212 for making patient-specific jigs.

In FIG. 1, a method 100 according to an embodiment may start at block 102. At block 102, a bone imaging machine generates a bone surface image from three-dimensional image data from the bone structure, such as the bones of the knee, of a patient. The bone surface image may include at least a portion of one or more of the femur, patella, tibia, and fibula. At block 104, a patient-specific device generator generates one or more prosthesis images superimposed on the bone surface image. The prosthesis image is positioned in its final, implanted position and orientation, regardless of the state of the patient's bone in the bone surface image. A mating surface of the prosthesis image may determine the surface of the resectioned knee bones of the patient. For example, by placing the prosthesis image in the final, implanted position and orientation, a surgeon may determine the final shape and orientation of the resectioned knee bone, for example, the femur, such that a prosthesis may be installed on the patient's resectioned femur in the correct, final, implanted position and orientation. The jigs created from the present disclosure may be designed to confirm proper resectioning of the knee bones during a knee replacement procedure.

At block 106, the patient-specific device generator generates a bone resection image. The bone resection image may include images of the bone surfaces on which a prosthesis is installed. The resection image may be generated according to the installation position of the prosthesis.

At block 108, the patient-specific device generator generates a patient-specific jig image superimposed proximate the bone resection image and the bone surface image. The patient-specific device generator may use the bone surface image and bone resection image to create a patient-specific device with anatomic engagement members that have an engagement surface that corresponds to, matches, or is the negative contour of the patient's anatomy.

At block 110, a patient-specific device converter generates control data from the patient-specific jig image. The control data may be in the form of a machine readable file, such as a g-code file, for controlling a manufacturing machine. The control data may be used by a machine during a manufacturing process to create physical patient-specific jigs by additive or subtractive machining, such as fused deposition modeling, stereolithography, or other methods. At block 112, the manufacturing device creates a physical patient-specific jig.

As discussed above, FIG. 2 shows one embodiment of the system 210 for carrying out the methods of FIG. 1 according to some aspects of the present disclosure. The computing system 212 may include instructions in the form of computer software for automatically generating images of prosthesis implants in final installation positions and patient-specific jigs on the bone structure images. In some aspects, it may be necessary for the surgeon during preoperative planning to input information into the input device 218 for creating or altering jig images or prostheses images for a particular patient based on the surgeon's understanding of the particular bone structure of the patient as displayed on the display device 216.

Figure 3:
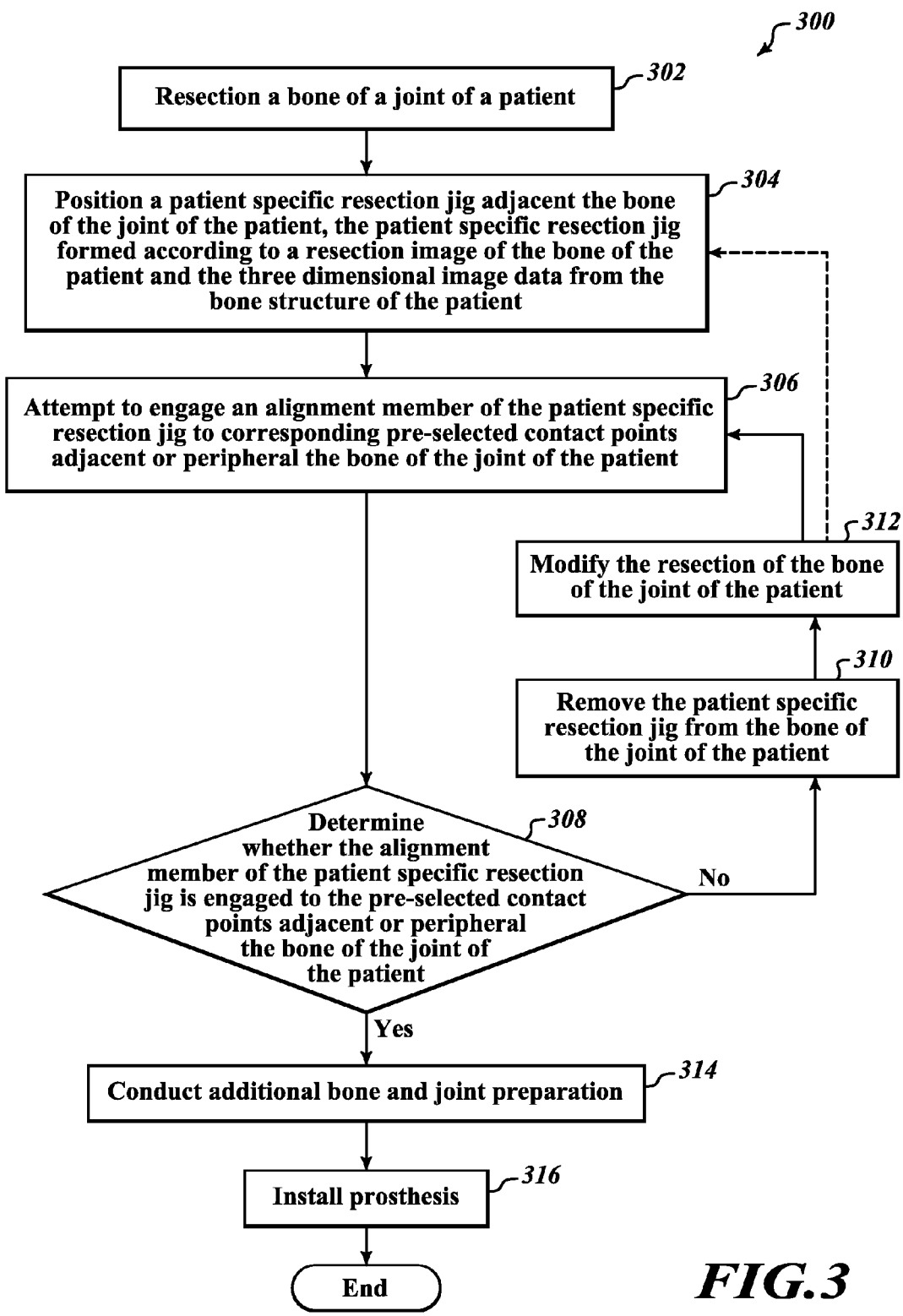
FIG. 3 depicts a method according to one or more embodiments disclosed herein.

FIG. 3 is a flow diagram of a method pertaining to operative surgery according to aspects of the present disclosure. The method of FIG. 3 may be carried out by a surgeon, by a machine, or by both. Moreover, the process may utilize some or all of the devices discussed with reference to FIGS. 1 and 2 during surgery, such as viewing the preoperative images displayed on the display device while operating on a patient.

FIG. 3 shows a method 300 according to an embodiment disclosed herein. The method 300 may be carried out using a patient-specific jigs, such as, for example, the patient-specific jigs shown in FIGS. 7, 8, 10, and 11. The method may start at block 302 with the resectioning of the knee bone. In full or total knee replacement procedures patients have their femur, tibia, and patella bones resectioned to accept a prosthetic. The resection process may include cutting, milling or any other method to prepare the surface of the bones to accept a prosthetic.

At block 304, a surgeon or machine may place a patient-specific resection jig adjacent the bone of the joint of the patient, the patient-specific resection jig formed according to a resection image of the bone of the patient and three-dimensional image data from the bone structure of a patient. Placing the patient-specific resection jig may include aligning an alignment surface with a resectioned surface of the bone or aligning an anatomic alignment member of the patient-specific jig to a corresponding preselected area adjacent or peripheral the resectioned bone portion of the patient. For example, a surgeon may position the patient-specific resection jig on the resectioned surface of the patient's bone and align, but possibly not engage, the various alignment members of the patient-specific resection jig with anatomical features adjacent the resectioned surfaces of a patient. The surgeon may also attempt to align the bone facing surfaces and a periphery of the patient-specific resection jig with the resection surface of the patient's bone and periphery thereof. By positioning the jig in such a manner, the surgeon may evaluate the initial resection cuts and determine whether adjustments should be made to the initial resection cuts before attempting to drill or otherwise create the prosthesis mounting holes or placing the prosthesis in its final or predetermined installation position. If the patient specific jig is too large or too small, the surgeon may confirm that too little or too much bone has been removed or that the previous cuts were made improperly.

At block 306, a surgeon or machine may attempt to engage an anatomical alignment member of the patient-specific jig corresponding to preselected areas adjacent to or on the periphery of the resectioned surface of the bone of the patient. At block 308, a surgeon or machine may determine whether the alignment members are engaged with the preselected contact points adjacent or peripheral the resectioned bone of the joint of the patient. The surgeon or a machine may also determine whether the bone facing surfaces and periphery of the patient-specific resection jig are engaged with or aligned with the resectioned surface of the bone of the patient and the periphery thereof. If the patient-specific resection jig is properly aligned and engaged with the bone, then the surgeon or machine may determine that the resection portion of the surgery is complete and may use the patient-specific jig as a guide for accurately conducting additional or final machining of the bone prior to placing a prosthesis. If the patient-specific resection jig is not properly aligned or engaged with the bone, the surgeon or machine may evaluate the misalignment or disengagement and determine how to adjust or account for the improperly resectioned bone surfaces. For example, a misalignment of one side of the patient-specific resection jig may indicate that the resection was cut at an incorrect angle. As an additional example, a patient specific jig that has a perimeter larger or smaller than the perimeter of a resection surface of the bone may convey that too littler or too much bone was removed and allow for a surgeon to consider changing the intraoperative plan.

In some embodiments, a surgeon may remove additional bone with a saw or other device and revise the initial bone cuts by cutting more bone. In other instances, a surgeon may accept the suboptimal bone cut or cuts and place additional bone cement in the area, augment the prosthesis to correct for the incorrect cut, or otherwise proceed to complete the planned surgical procedure.

If the resection was incorrectly performed and the patient-specific resection jig does not align or engage properly with the patient's bone, then the decision at block 308 may proceed to block 310.

At block 310, the patient-specific resection jig is removed from the bone of the joint of the patient. Here, the surgeon or a machine may remove the jig from the patient and proceed to block 312.

At block 312, the surgeon or a machine may modify the resection of the bone of the joint of the patient. In full or total knee replacement procedures a surgeon may perform additional bone removal or resection procedures on the femur, tibia, or patella bones to correct the previous resection attempts. The additional resection process may include cutting, milling or any other method to prepare the surface of the bones to accept a prosthetic. The actions performed at block 312 may be similar to the actions performed early at block 302. These actions may include, for example, positioning a resection guide at the patient's joint to aid in performing the resection or bone removal procedures.

The method may then proceed back to block 306, as shown in FIG. 3, where a surgeon or machine may again attempt to engage an anatomical alignment member of the patient-specific jig corresponding to preselected areas adjacent to or on the periphery of the resectioned surface of the bone of the patient. In some embodiments, the method may proceed from block 312 back to block 304 where the surgeon or machine may again place a patient-specific resection jig adjacent the bone of the joint of the patient, the patient-specific resection jig formed according to a resection image of the bone of the patient and three-dimensional image data from the bone structure of a patient before proceeding again to block 306 and eventually to block 308.

At block 308, the surgeon or machine evaluates the resection and preparation of the bone for receiving a prosthesis. The alignment and engagement of the patient-specific resection jig is evaluated. If the alignment members of the patient-specific resection jig engage with the preselected contact points or areas adjacent or peripheral the bone of the joint of the patient, then the procedure may proceed to block 314.

At block 314, a surgeon or machine conducts additional bone and joint preparation actions. In some embodiments, a patient-specific resection jig may include guide holes for creating lug holes in a patient's bone, such as the femur, for mounting a prosthetic, guides or guide surfaces to assist in cutting the intercondylar notch area of the femur for posterior cruciate substituting knee replacement techniques, and guide holes for creating a cavity for receiving a stem of the tibial prosthesis. The surgeon or machine may use drills, mills, saws, broaches, or other tools when undertaking the additional preparatory actions at block 314.

At block 316, a surgeon or machine installs the prosthesis. One or more prostheses may be installed, including a femoral prosthesis, tibular prosthesis, or patellar prosthesis.

Figure 4:
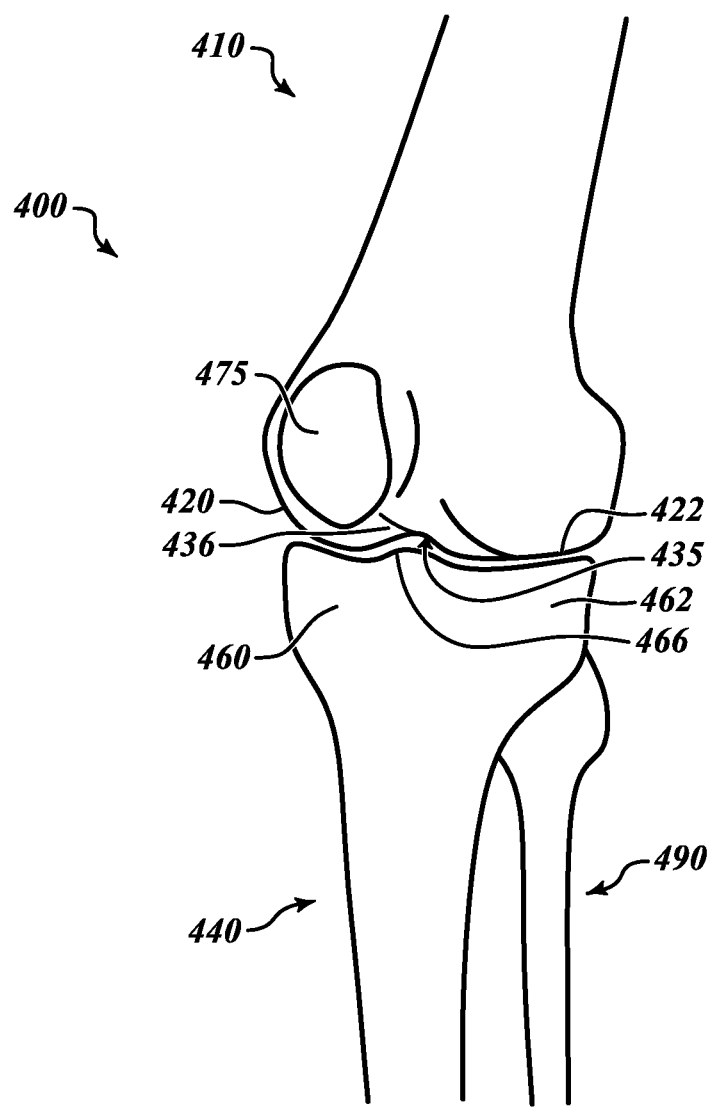
FIG. 4 depicts a knee joint and the bones associated therewith.

FIG. 4 shows a knee joint 400 and the bones associated with the knee joint. The knee joint includes four bones, the femur 410, the tibia 440, the fibula 490, and the patella 475. In knees most partial and full knee replacement surgeries of one or more of the femur 410, the tibia 440 and the patella 475 are modified while the fibula is usually not directly modified during the surgery. The lower or distal end of the femur 410 includes lateral (outer) femoral condyle 422 and medial (inner) femoral condyle 420. The femoral condyle 420, 422 are weight bearing projections that ride on the meniscus, not shown, of the knee. The meniscus is located between the lower end of the femur 410 and the upper end of the tibia 440 and acts to reduce friction in and load on the knee. The intercondylar fossa 435 is the depression at the end of the femur 410 between the femoral condyle 420, 422. The posterior cruciate ligament (PCL) and the anterior cruciate ligament (ACL), not shown, attach to the femur 410 in the intercondylar fossa 435. The femur also includes the patellar groove or surface 436. The patellar groove 436 is located on the front of the femur 410 and behind the patella 475. The patella 475 rides in the patellar groove 436 as the knee joint 400 bends and straightens.

The tibia 440 includes a medial tibia condyle 460 and a lateral tibia condyle 462. The tibia condyles 460, 462 bear the forces imparted by the corresponding femoral condyles 420, 422. The tibia 440 also includes an intercondylar eminence 466, located between the tibia condyles 460, 462. The ACL and PCL attach to the tibia 440 in front of and behind the intercondylar eminence 466.

Figure 5:
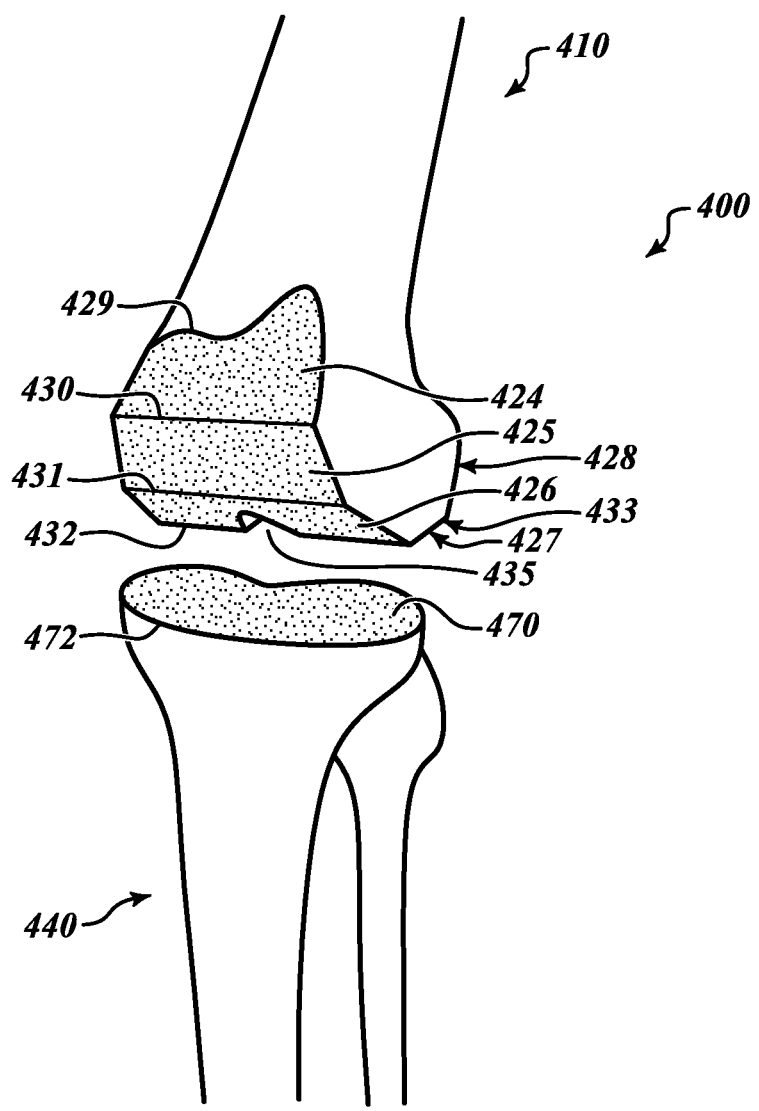
FIG. 5 depicts a sectioned femur and a sectioned tibia according on one or more embodiments disclosed herein.

FIG. 5 shows a resectioned knee joint 400 with the patella omitted for clarity. FIG. 5 shows an example of what a knee may typically look like after the initial resectioning of the femur 410 and tibia 440 according to a preoperative plan by either traditional techniques using extramedullary or intramedullary guides or other known techniques. This is how a knee may look, for example, after the resection procedure at block 302 of the method 300. The femur 410 and tibia 440 show a resection according to a total knee replacement where the patient has their femur, tibia, and patella bones resectioned to accept a prosthetic. The resection process may include cutting, milling or any other method to prepare the surface of the bones to accept a prosthetic.

The femur 410 includes five resectioned surfaces, the anterior resectioned surface 424, anterior-distal resectioned surface 425, the distal resectioned surface 426, the posterior-distal resectioned surface 427, and the posterior resectioned surface 428. Each resectioned surface 424, 425, 426, 427, 428 is bounded by an edge. For example, a perimeter 429 delineates the boundary between the resectioned surfaces 424, 425, 426, 427, 428 and the unmodified bone of the femur, while vertices 430, 431, 432, 433 form the edges between adjacent resectioned surfaces 424, 425, 426, 427, 428. The posterior portion of the intercondylar fossa 435 is also visible in this view.

Although depicted at having five resectioned surfaces, in some embodiment the femur 410 may have more than five resectioned surfaces or less than five resectioned surfaces.

During the resectioning of the femur 410 in a total knee replacement, a surgeon or machine removes at least a portion of, and in many cases all of the medial condyle 420, lateral femoral condyle 422, the patellar groove 436, and the intercondylar fossa 435 to prepare the femur 410 to accept a femoral prosthesis or implant. In a partial knee replacement, a smaller portion of the femur 410 is removed, for example, only the medial or lateral condyle of the lower end of the femur 410 is resectioned.

While resectioning the femur may involve a number or cuts to create several resectioned surfaces 424, 425, 426, 427, 428, the tibia 440 may only include a single resectioned surface 470 surrounded by a perimeter 472 to accept a tibia prosthesis or implant. The resectioning of the tibia 440 for total knee replacement may include removing the upper surface of the tibia 440, including the medial tibia condyle 460, the lateral tibia condyle 462, and the intercondylar eminence 466. In a partial knee replacement, a smaller portion of the tibia 440 is removed. For example, only the medial or lateral half of the upper end of the tibia 440 is resectioned.

Figure 6:
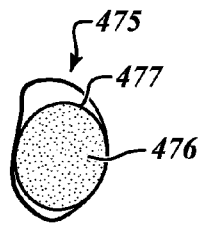
FIG. 6 depicts a sectioned patella according on one or more embodiments disclosed herein.

FIG. 6 shows the posterior view of the patella 475 after resection. The resectioned surface 476 of the patella 475 is surrounded by an edge 477 between the resectioned surface 476 of the bone and the unmodified portion of the patella 475. Although depicted as substantially round, in some embodiments the shape of the resectioned surface 476 of the patella 475 is not round. Indeed, the shape of the resectioned surface 476 of the patella 475 differs from patient to patient, as does the resectioned surfaces of the femur 410 and tibia 440.

After the surgeon or machine resections the bones a surgeon may insert a patient-specific resection jig into the patient. A patient-specific resection jig, such as the patient-specific femoral resection jig 600 shown in FIG. 7 may be designed and manufactured based on a patient femur 410 and the preoperatively planned resection surfaces 424, 425, 426, 427, 428 made to the femur 410. The patient-specific femoral resection jig 600 aids in verifying the resection cuts made to the femur 410 and in preparing the femur 410 to accept a prostheses in PCL preserving knee replacement procedures. The patient-specific femoral resection jig 600 can be developed as either a physical component via a prototyping machine or visual representations in a 3D modeling software program based upon the 3D images of the patient.

The patient-specific femoral resection jig 600 includes a body that is shaped to conform to the shape of the resectioned femur 410. For example, the body of the patient-specific femoral resection jig 600 includes a bone facing side 640 that includes one or more bone facing surfaces 641, 642, 643, 644, 645. Each of the bone facing surfaces 641, 642, 643, 644, 645 are shaped to match a corresponding resection surface 424, 425, 426, 427, 428, based on the preoperative planning. If the surgeon performed the resection procedure correctly, as determined by the preoperative plan, then each of the bone facing surfaces 641, 642, 643, 644, 645 should match or contact the corresponding resection surface. For example, the first bone facing surface 641 should match or contact the resection surface 424. One or more of the bone facing surfaces 641, 642, 643, 644, 645 may have an orientation or angle different than the orientation or angle of another bone facing surface 641, 642, 643, 644, 645.

If the surgeon performed the resection procedure and did not make the resection cuts in accordance with the preoperative plan, then the bone facing surfaces 641, 642, 643, 644, 645 may not match the corresponding resection surfaces 424, 425, 426, 427, 428 or there may be a size mismatch between the bone facing surfaces of the patient-specific jig and the and the patient's resectioned bone. When this happens, the patient-specific femoral resection jig 600 may indicate information to the surgeon regarding the resection surfaces. For example, if the resection cut for the first resection surface 424 did not remove enough of the femur 410, then the bone facing surfaces 641 may contact the first resection surface 424, but this contact may prevent the other bone facing surfaces 642, 643, 644, 645 from contacting or otherwise aligning with their corresponding resection surfaces 425, 426, 427, 428.

Similarly, if the resection cut for the first resection surface 424 removed too much of the femur 410, then the bone facing surfaces 641 may not contact the first resection surface 424, while, if the rest of the resection cuts were correctly made, then the other bone facing surfaces 642, 643, 644, 645 may still contact or otherwise align with their corresponding resection surfaces 425, 426, 427, 428.

The patient-specific femoral resection jig 600 may also include a perimeter alignment feature, such as the alignment perimeter 610. As shown in FIG. 5, the resectioned surfaces 424, 425, 426, 427, 428 are bounded by a perimeter 429. The perimeter 429 is created during the resectioning process and may be determined during preoperative planning based on the patient's particular bone geometry and the location, depth, and orientation of each of the resection surfaces that the surgeon plans to make to the femur 410.

The shape of the alignment perimeter 610 may also be determined during preoperative planning. The shape of the alignment perimeter 610 matches the shape of the perimeter 429 of a properly resectioned femur 410 according to the preoperative plan. During a knee replacement procedure, a surgeon or machine may place the patient-specific femoral resection jig 600 against the femur 410 and attempt to align the alignment perimeter 610 with the perimeter 429 of the resectioned surfaces 424, 425, 426, 427, 428. If the alignment perimeter 610 does not align with the perimeter 429 of the resectioned surfaces 424, 425, 426, 427, 428, then the surgeon knows that they may need to perform remedial work on the resectioned surfaces 424, 425, 426, 427, 428, or otherwise account for the resectioned surfaces 424, 425, 426, 427, 428 not matching the preoperative plan.

In some embodiments, the surgeon may perform additional resection cuts on the femur 410 to correct the resection surfaces so that the surfaces match the preoperative plan. To help the surgeon, the position and misalignment of the alignment perimeter 610 may indicate information to the surgeon or machine regarding the resectioned surfaces 424, 425, 426, 427, 428. For example, if the alignment perimeter 610 is outside the perimeter 429 of the resectioned surfaces 424, 425, 426, 427, 428, then the surgeon or machine may determine that the resection cut removed too much bone and the surgeon or machine may determine that shims should be added to the prosthesis to account for the excess bone removal. If the alignment perimeter 610 is inside the perimeter 429 of the resectioned surfaces 424, 425, 426, 427, 428, the surgeon or machine may determine that the resection cut removed too little bone and the surgeon or machine may determine that additional resection cuts should be made to the femur 410.

The patient-specific femoral resection jig 600 may also include one or more alignment members, such as the alignment members 620 extending from a periphery of the body of the patient-specific femoral resection jig 600. The alignment members 620 include an alignment surface 622 that conforms or matches the anatomic surface structure of the bone of the patient. For example, one or more alignment members 620 may align or engage with a point or area on the distal end of the femur 410 or adjacent the resection surface according to the three dimensional data of the bone structure of the patient. The alignment surface 622 may include a surface shape or contours that match the surface shape or contours of the anatomic structure with which the alignment member 620 aligns.

The shape and contours of the alignment surface 622 may be determined based upon the 3-D modeling images of the patient, a combination of two-dimensional radiographic images of the patient, or a combination of three-dimensional and two-dimensional images of a patient. The shape of the alignment surface 622 may also be referred to as a negative of the anatomic structure with which the alignment surface 622 aligns or engages. It is a negative because, for example, a protrusion on the distal end of the femur 410 would correspond to a depression on the alignment surface 622 while a depression on the distal end of the femur 410 would correspond to a protrusion on the alignment surface 622. Although depicted as having four alignment members, each with a single alignment surface, in some embodiments, a patient-specific femoral resection jig may have more or less than four alignment members and each may have more than one alignment surface. In some embodiments, a patient-specific femoral resection jig may have no alignment members.

The alignment members 620 and the alignment surfaces 622 may also provide information to the surgeon regarding the resection of the bone of the patient. For example, the alignment members 620 and the alignment surfaces 622 provide information to the surgeon regarding whether the bone has been properly or improperly resectioned. For example if any one of the alignment members 620 or the alignment surfaces 622 associated with the alignment members 620 is not making contact with the patient's bone, the surgeon may decide to perform a different resection, reposition the patient-specific femoral resection jig 600, or accept the imperfection and proceed with further surgery.

In PCL preserving knee replacement procedures, the patient-specific femoral resection jig 600 may include guides for creating features for mounting a prosthesis to the femur 410. For example, the patient-specific femoral resection jig 600 includes guide holes 630. The guide holes 630 are positioned and shaped according to the preoperative plan and the final installation position of the prosthesis and aid in guiding a surgical tool for creating mounting holes or cavities.

In addition to being in the correct position and shape for the proper placement of the mounting holes or cavities, the guides may include a surface guide to aid in creating the cavity or hole at the correct angle. For example, if the surface guides 631 are perpendicular to the resectioned surface 643, then they can guide a tool in a perpendicular direction into the femur 410 to create the cavity or hole. By using guides that have other angles with respect to the resectioned surface, a surgeon or machine can create cavities or holes at other angles.

Figure 7:
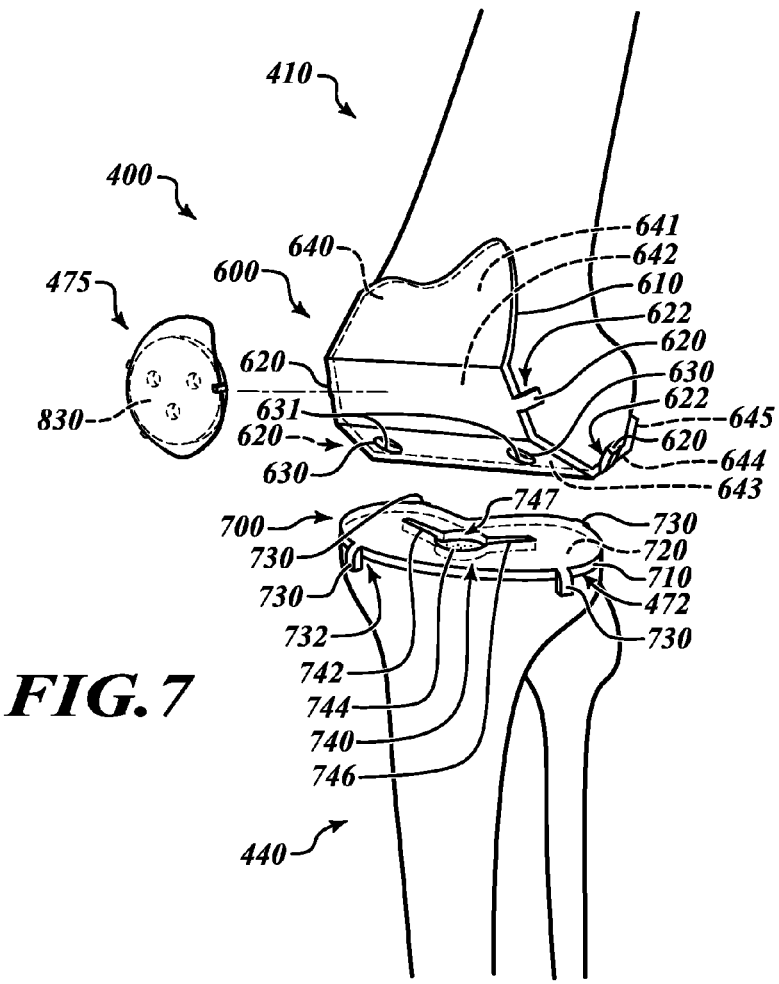
FIG. 7 depicts patient-specific jigs for knee replacement installed on the bones of the knee according to one or more embodiments disclosed herein.

FIG. 7 also depicts a patient-specific tibia resection jig 700 designed and manufactured based on a patient tibia 440 and the preoperatively planned resection surface 470 made to the tibia 440. The patient-specific tibia resection jig 700 aids in verifying the resection cut made to the tibia 440 and in preparing the tibia 440 to accept a prostheses. The patient-specific tibia resection jig 700 can be developed as either a physical component via a prototyping machine or as visual representations in a 3D modeling software program based upon the 3D images of the patient.

The patient-specific tibia resection jig 700 includes a body that is shaped to conform to the shape of the resectioned tibia 440. For example, the body of the patient-specific tibia resection jig 700 includes a bone facing side defined by at least one bone facing surface 720. The bone facing surface 720 is shaped to match a corresponding resection surface 470 of the tibia 440 based on the preoperative plan. Although the patient-specific tibia resection jig 700 shown in FIG. 7 includes a single bone facing surface 720, in some embodiments, the body of the patient-specific tibia resection jig 700 may contain more than one bone facing surface 720. If the surgeon performed the resection procedure correctly, then the bone facing surface 720 should match or contact the corresponding resection surface 470.

If the surgeon performed the resection procedure and did not make the resection cut in accordance with the preoperative plan, then the bone facing surface 720 may not match the corresponding resection surface 470. When this happens, the patient-specific tibia resection jig 700 may indicate information to the surgeon regarding the resection surfaces. For example, if the resection cut for the resection surface 470 is not flat or in a single plane, then the bone facing surface 720 may contact a portion of the resection surface 470, but not contact other portions of the of the resection surface 470. In such a situation, the patient-specific tibia resection jig 700 may indicate to the surgeon the locations on the resection surface 470 of the tibia 440 where additional bone material should be removed such that the resection surface 470 may match the surface prescribed in the preoperative plan.

The patient-specific tibia resection jig 700 may also include a perimeter alignment feature, such as the alignment perimeter 710. The resectioned surface 470 is bounded by a perimeter 472. The perimeter 472 is created during the resectioning process and may be determined during preoperative planning based on the patient's particular bone geometry and the location, depth, and orientation of the resection surface 470 of the tibia 440.

The shape of the alignment perimeter 710 may also be determined during preoperative planning. The shape of the alignment perimeter 710 matches the shape of the perimeter 472 of a properly resectioned tibia 440 according to the preoperative plan. During a knee replacement procedure, a surgeon or machine may place the patient-specific tibia resection jig 700 against the tibia 440 and attempt to align the alignment perimeter 710 with the perimeter 472 of the resectioned surface 470. If the alignment perimeter 710 does not align with the perimeter 472 of the resectioned surface 470, then the surgeon knows that they may need to perform additional remedial work on the resectioned surface 470, or to otherwise account for the resectioned surfaces 470 not matching the preoperative plan.

In some embodiments, the surgeon may perform additional resection cuts on the tibia 440 to correct the resection surface 470 so that the surface matches the preoperative plan. To help the surgeon, the position and misalignment of the alignment perimeter 710 may indicate information to the surgeon or machine regarding the resectioned surface 470. For example, if the alignment perimeter 710 is inside the perimeter 472 of the resectioned surface 470, then the surgeon or machine may determine that the resection cut removed an inadequate amount of bone and more bone may need to be removed. If the alignment perimeter 710 is outside the perimeter 472 of the resectioned surface 470, then the surgeon or machine may determine that too much bone was resected and the surgeon or machine may use an augmented prosthesis, additional cement, determine that additional resection cuts should be made, or use other methods to make accommodations for the incorrect resection.

The alignment perimeter 710 may also indicate that the resection surface 470 was cut at an incorrect angle. For example, a portion of the alignment perimeter 710 on a first side of the patient-specific tibia resection jig 700 may align with the outside the perimeter 472 of the resectioned surface 470, but a second side of the patient-specific tibia resection jig 700 may not align with the outside the perimeter 472 of the resectioned surface 470. This type of partial alignment may indicate that the resection of the tibia 440 was performed at an angle other than that prescribed in the preoperative plan.

The patient-specific tibia resection jig 700 may also include one or more alignment members, such as the alignment members 730 extending from a periphery of the body of the patient-specific tibia resection jig 700. The alignment members 730 include an alignment surface 732 that conforms or matches the anatomic surface structure of the bone of the patient. For example, one or more alignment members 730 may align or engage with a point or area on the proximal end of the tibia 440 or adjacent the resection surface to the three dimensional data of the bone structure of the patient. The alignment surface 732 may include a surface shape or contours that match the surface shape or contours of the anatomic structure with which the alignment member 730 aligns.

The shape and contours of the alignment surface 732 may be determined based upon the 3-D modeling images of the patient, a combination of two-dimensional radiographic images of the patient, or a combination of three-dimensional and two-dimensional images of a patient. The shape of the alignment surface 732 may also be referred to as a negative of the anatomic structure with which the alignment surface 732 aligns or engages.

The alignment members 730 and the alignment surfaces 732 may also provide information to the surgeon regarding the resection of the bone of the patient. For example, the alignment members 730 and the alignment surfaces 732 provide information to the surgeon regarding whether the bone has been properly or improperly resectioned. For example if any one of the alignment members 730 or the alignment surfaces 732 associated with the alignment members 730 is not making contact with the patient's bone, the surgeon may decide to perform a different resection, reposition the patient-specific tibia resection jig 700, or accept the imperfection and proceed with further surgery.

Although depicted as having four alignment members, each with a single alignment surface, in some embodiments, the patient-specific tibia resection jig 700 may have more or less than four alignment members 730 and each may have more than one alignment surface 732. In some embodiments, the patient-specific tibia resection jig 700 may have no alignment members 730.

The patient-specific tibia resection jig 700 may include guides for creating features for mounting a prosthesis to the tibia 440. For example, the patient-specific tibia resection jig 700 includes guide hole 740. The guide hole 740 is positioned and shaped according to the preoperative plan and aids in guiding a surgical tool for creating mounting holes or cavities for attaching the tibial component to the tibia 440 in a final installation position. The guide hole 740 may include a primary guide 744 and secondary guides 742, 746. The primary guide 744 may aid in guiding a tool for creating a hole or cavity for receiving the main body of the tibial component's mounting stem while the secondary guides 742, 746 aid in creating a hole or cavity for receiving the stabilizing extension members of the tibial component.

In addition to being in the correct position and shape for the proper placement of the mounting holes of cavities, the guides may include a surface guide to aid in creating the cavity or hole at the correct angle. For example, if the surface guide 747 is perpendicular to the resectioned surface 470, then the surface guide 747 can guide a tool in a perpendicular direction into the tibia 440 to create the cavity or hole. By using guides that have other angles with respect to the resectioned surface, a surgeon or machine can create cavities or holes at other angles.

Figure 8:
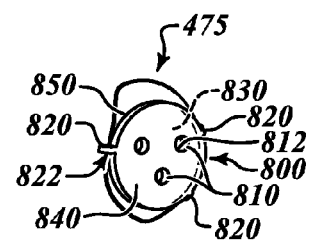
FIG. 8 depicts a patient-specific patella jig installed according to one or more embodiments disclosed herein.

FIG. 8 depicts a patient-specific patella resection jig 800 designed and manufactured based on a patient patella 475 and the preoperatively planned resection surface 476 made to the patella 475. The patient-specific patella resection jig 800 aids in verifying the resection cut made to the patella 475 and in preparing the patella 475 to accept a prostheses. The patient-specific patella resection jig 800 can be developed as either a physical component via a prototyping machine or as visual representations in a 3D modeling software program based upon the 3D images of the patient.

The patient-specific patella resection jig 800 includes a body 840 that is shaped to conform to the shape of the resectioned patella 475. For example, the body 840 of the patient-specific patella resection jig 800 includes a bone facing side defined by at least one bone facing surface 830. The bone facing surface 830 is shaped to match a corresponding resection surface 476 of the patella 475 based on the preoperative plan. Although the patient-specific patella resection jig 800 shown in FIG. 8 includes a single bone facing surface 830, in some embodiments, the body 840 of the patient-specific patella resection jig 800 may contain more than one bone facing surface 830. If the surgeon performed the resection procedure correctly, then the bone facing surface 830 should match or contact the corresponding resection surface 476.

As with the tibia and femur resection procedures and jigs, if the surgeon performed the resection procedure and did not make the resection cut in accordance with the preoperative plan, then the bone facing surface 830 of the patient-specific resection jig 800 may not match the corresponding resection surface 476 of the patella 475. When this happens, the patient-specific patella resection jig 800 may indicate information to the surgeon regarding the resection surface. For example, if the resection cut for the resection surface 476 is not flat or in a single plane, then the bone facing surface 830 may contact a portion of the resection surface 476, but not contact other portions of the resection surface 476. In such a situation, the patient-specific patella resection jig 800 may indicate to the surgeon the locations on the resection surface 476 of the patella 475 where additional bone material should be removed such that the resection surface 476 may match the surface prescribed in the preoperative plan or where additional cement may be used to compensate for an incorrect resection.

The patient-specific patella resection jig 800 may also include a perimeter alignment feature, such as the alignment perimeter 850. The resectioned surface 476 is bounded by a perimeter 477. The perimeter 477 is created during the resectioning process and may be determined during preoperative planning based on the patient's particular bone geometry and the location, depth, and orientation of the resection surface 476 of the patella 475.

The shape of the alignment perimeter 850 may also be determined during preoperative planning. The shape of the alignment perimeter 850 matches the shape of the perimeter 477 of a properly resectioned patella 475 according to the preoperative plan. During a knee replacement procedure, a surgeon or machine may place the patient-specific patella resection jig 800 against the patella 475 and attempt to align the alignment perimeter 850 with the perimeter 477 of the resectioned surface 476. If the alignment perimeter 850 does not align with the perimeter 477 of the resectioned surface 476, then the surgeon knows that they may need additional remedial work on the resectioned surface 476, or to otherwise account for the resectioned surface 476 not matching the preoperative plan, for example, as described above with respect to the femur 410 and tibia 440. A size mismatch of the patella jig to the cut patella may indicate that either too much bone or not enough bone has been removed.

The patient-specific patella resection jig 800 may also include one or more alignment members, such as the alignment members 820 extending from a periphery of the body of the patient-specific patella resection jig 800. The alignment members 820 include an alignment surface 822 that conforms or matches the anatomic surface structure of the bone of the patient. For example, one or more alignment members 820 may align or engage with a point or area adjacent to the resection surface 476 of the patella 475 to the three dimensional data of the bone structure of the patient. The alignment surface 822 may include a surface shape or contours that match the surface shape or contours of the anatomic structure with which the alignment member 820 aligns.

The alignment members 820 and the alignment surfaces 822 may also provide information to the surgeon regarding the resection of the bone of the patient. For example, the alignment members 820 and the alignment surfaces 822 provide information to the surgeon regarding whether the bone has been properly or improperly resectioned. For example if any one of the alignment members 820 or the alignment surfaces 822 associated with the alignment members 820 is not making contact with the patient's bone, the surgeon may decide to perform a different resection, reposition the patient-specific patella resection jig 800, or accept the imperfection and proceed with further surgery.

The shape and contours of the alignment surface 822 may be determined based upon the 3-D modeling images of the patient, a combination of two-dimensional radiographic images of the patient, or a combination of three-dimensional and two-dimensional images of a patient. The shape of the alignment surface 822 may also be referred to as a negative of the anatomic structure with which the alignment surface 822 aligns or engages.

Although depicted as having three alignment members 820, each with a single alignment surface, in some embodiments, the patient-specific patella resection jig 800 may have more or less than three alignment members 820 and each may have more than one alignment surface 822. In some embodiments, the patient-specific patella resection jig 800 may have no alignment members 820.

The patient-specific patella resection jig 800 may include guides for creating features for mounting a prosthesis to the patella 475. For example, the patient-specific patella resection jig 800 includes three guide holes 810. The guide holes 810 are positioned and shaped according to the preoperative plan and aid in guiding a surgical tool for creating mounting holes or cavities for attaching the patella component to the patella 475 according to the preoperative plan. In some embodiments, the patient-specific patella resection jig 800 may include more or fewer guide holes 810. Various surgical tools may be used to further machine the patella for acceptance of a final prosthesis or prior to placing a final prosthesis.

In addition to being in the correct position and shape for the proper placement of the mounting holes or cavities, the guides may include a guiding surface 812 to aid in creating the cavity or hole at the correct angle. For example, if the guiding surface 812 is perpendicular to the resectioned surface 476, then the guiding surface 812 can guide a tool in a perpendicular direction into the patella 475 to create the cavity or hole. By using guides that have other angles with respect to the resectioned surface, a surgeon or machine can create cavities or holes at other angles.

Figure 9:
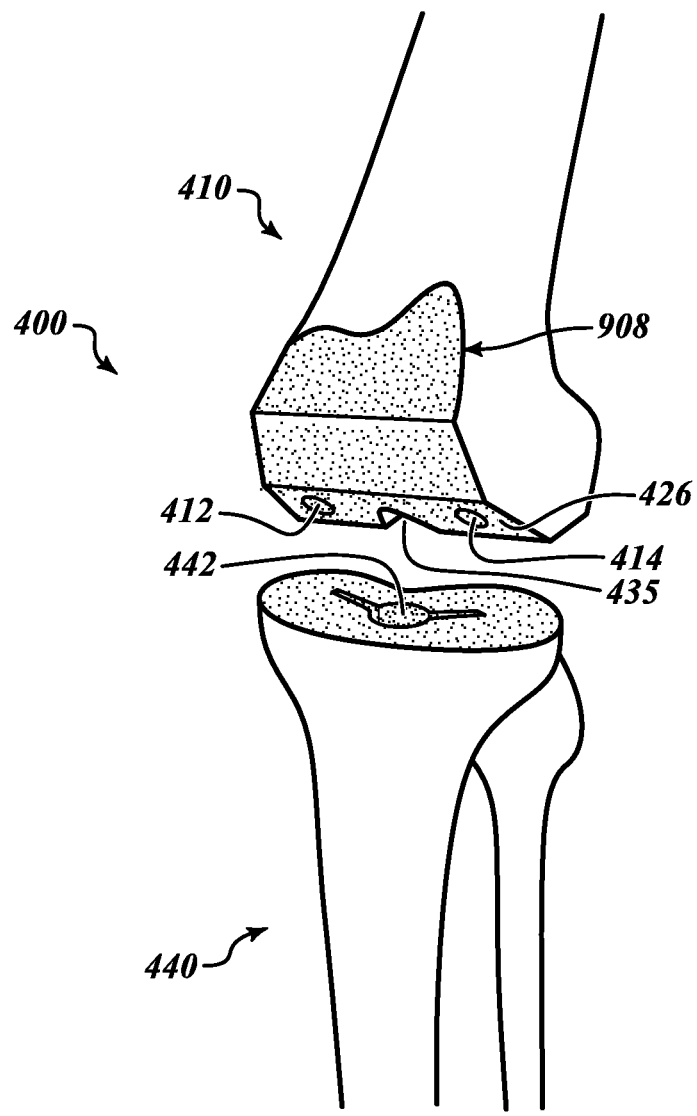
FIG. 9 depicts a sectioned knee bones according to one or more embodiments disclosed herein.

FIG. 9 depicts an embodiment of a knee joint 400 after resectioning the ends of the femur 410 and tibia 440, creating the mounting cavities 412, 414, 442 for the femoral and tibia components in a PCL preserving knee replacement procedure. As shown in FIG. 9, the posterior portion of intercondylar fossa 435 remains intact which preserves PCL attachment to the femur 410. FIG. 9 shows how the femur 410 and the tibia 440 would look during a knee replacement procedure before installation of the femoral and tibia components.

Figure 10:
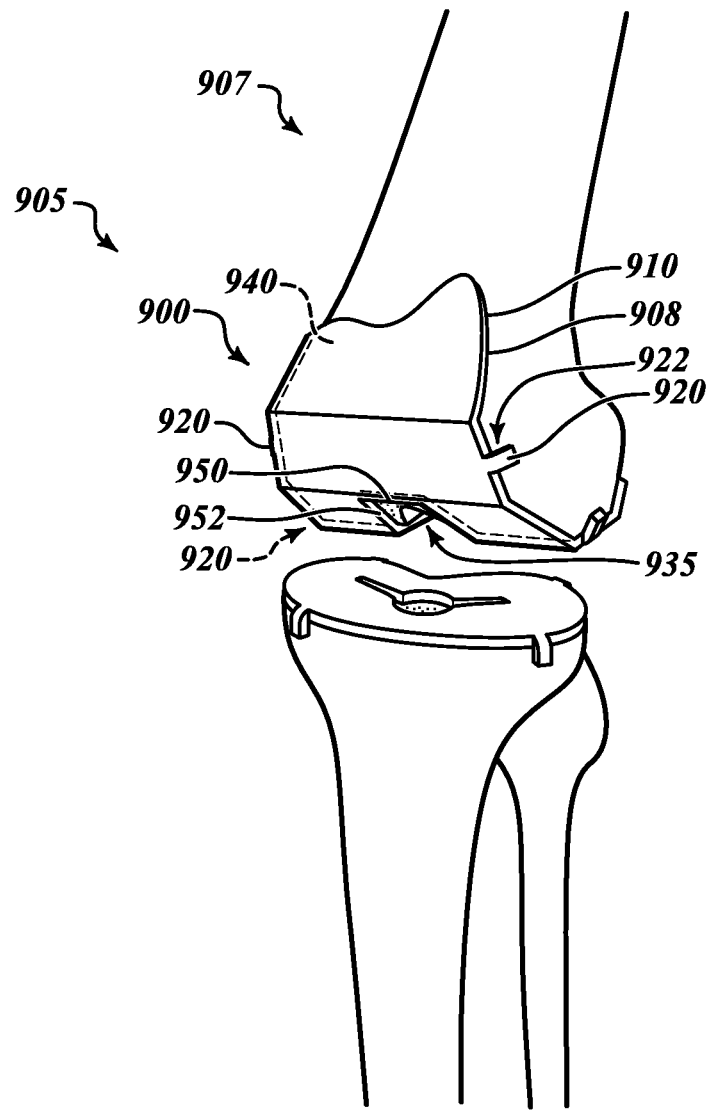
FIG. 10 depicts patient-specific jigs for knee replacement according to one or more embodiments disclosed herein.

The patient-specific femoral resection jig 900, shown as engaged with the femur 907 of the knee joint 905 in FIG. 10, is an embodiment of a jig used in PCL sacrificing knee replacement procedures. The patient-specific femoral resection jig 900 aids in verifying the resection cut made to the femur 907 and in preparing the femur 907 to accept a prostheses. The patient-specific femoral resection jig 900 can be developed as either a physical component via a prototyping machine or as visual representations in a 3D modeling software program based upon the 3D images of the patient.

The patient-specific removal resection jig 900 includes a body that is shaped to conform to the shape of the resectioned femur 907. For example, the body of the patient-specific removal resection jig 900 includes a bone facing side defined by at least one bone facing surface 940. The bone facing surface 940 is shaped to match a corresponding resection surface of the femur 907 based on the preoperative plan. If the surgeon performed the resection procedure correctly, the bone facing surface 940 should match or contact the corresponding resection surface.

If the surgeon performed the resection procedure and did not make the resection cut in accordance with the preoperative plan, the bone facing surface 940 of the patient-specific femoral resection jig 900 may not match the corresponding resection surface of the femur 907. When this happens, the patient-specific femoral resection jig 900 may indicate information to the surgeon regarding the resection surface. For example, the patient-specific femoral resection jig 900 may indicate to the surgeon the locations on the resection surface of the femur 907 where bone material should be removed such that the resection surface may match the surface prescribed in the preoperative plan. In some embodiments, the patient-specific femoral resection jig 900 may indicate that too little or too much bone was removed during resection or that the resection cut was made at an incorrect angle. By attempting to align the bone facing surface 940 with the resectioned surface of the femur 907, the patient-specific femoral resection jig 900 may indicate to the surgeon how the surface was missectioned and may aid the surgeon in determining appropriate corrective actions to fix or account for the incorrectly sectioned femur 907. In some embodiments, the surgeon may accept the imperfection and proceed with surgery. In some embodiments, the surgeon may augment the prosthesis or add additional cement to account for the imperfection, or in some embodiments proceed in another manner.

The patient-specific femoral resection jig 900 may also include a perimeter alignment feature, such as the alignment perimeter 910. The resectioned surface of the femur 907 is bounded by a perimeter 908. The perimeter 908 is created during the resectioning process and may be determined during preoperative planning based on the patient's particular bone geometry and the location, depth, and orientation of the resection surface of the femur 907.

The shape of the alignment perimeter 910 may also be determined during preoperative planning. The shape of the alignment perimeter 910 matches the shape of the perimeter 908 of a properly resectioned femur bone 907 according to the preoperative plan. During a knee replacement procedure, a surgeon or machine may place the patient-specific femur resection jig 900 against the femur 907 and attempt to align the alignment perimeter 910 with the perimeter 908 of the resectioned femur 907. If the alignment perimeter 910 does not align with the perimeter 908 of the resectioned femur 907, the surgeon knows that they may need to perform remedial work on the resectioned surface, or to otherwise account for the resectioned surface not matching the preoperative plan.

The patient-specific femur resection jig 900 may also include one or more alignment members, such as the alignment members 920 extending from a periphery of the body of the patient-specific femoral resection jig 900. The alignment members 920 include an alignment surface 922 that conforms to or matches the anatomic surface structure of the bone of the patient. For example, one or more alignment members 920 may align or engage with a point or area adjacent to the resection surface of the femur 907 to the three dimensional data of the bone structure of the patient. The alignment surface 922 may include a surface shape or contours that match the surface shape or contours of the anatomic structure with which the alignment member 920 aligns.

The shape and contours of the alignment surface 922 may be determined based upon the 3-D modeling images of the patient, a combination of two-dimensional radiographic images of the patient, or a combination of three-dimensional and two-dimensional images of a patient. The shape of the alignment surface 922 may also be referred to as a negative of the anatomic structure with which the alignment surface 922 aligns or engages.

Although depicted as having four alignment members 920, each with a single alignment surface, in some embodiments, the patient-specific femoral resection jig 900 may have more or less than four alignment members 920 and each may have more than one alignment surface 922. In some embodiments, the patient-specific femoral resection jig 900 may have no alignment members 920.

The patient-specific femoral resection jig 900 may include guides for creating features for mounting a prosthesis to the femur 907 or for removing the posterior portion of the intercondylar fossa 935. For example, the patient-specific femoral resection jig 900 includes an intercondylar fossa removal guide 950 with at least one intercondylar fossa removal guide surface 952. The guide surface 952 is positioned and shaped according to the preoperative plan and aids in guiding a surgical tool for removing the posterior portion of the intercondylar fossa 935. During the knee replacement procedure, a surgeon may guide a cutting blade or tool using the intercondylar fossa removal guide 950 and intercondylar fossa removal guide surface 952.

Figure 11:
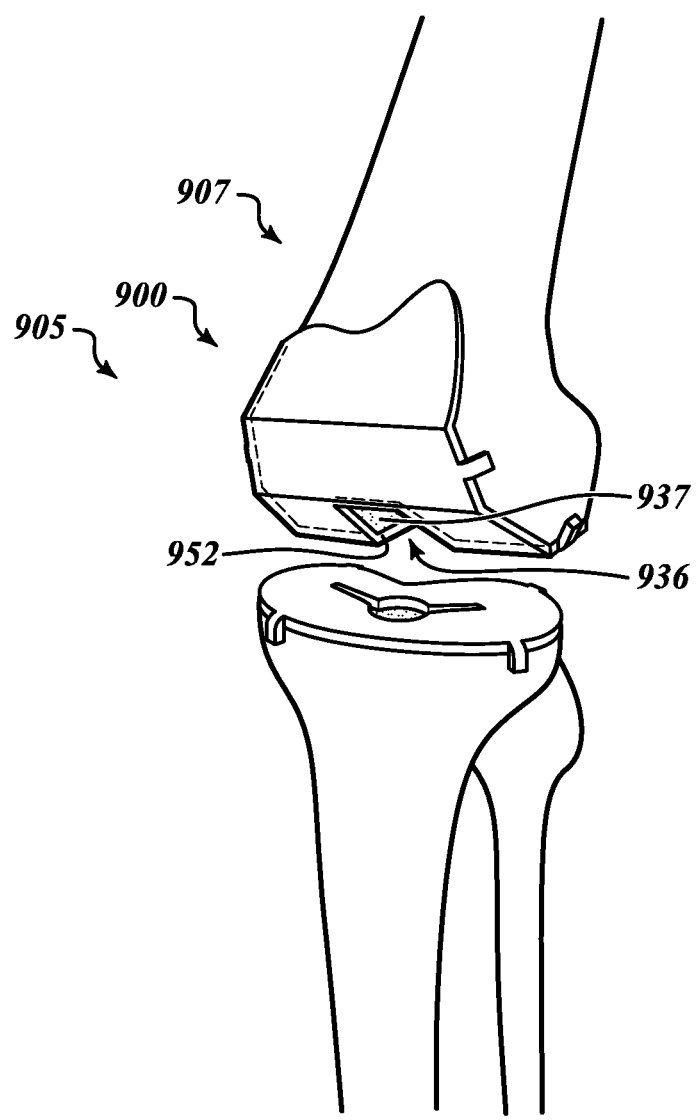
FIG. 11 depicts sectioned knee bones and patient-specific jigs according to one or more embodiments disclosed herein.

FIG. 11 depicts an embodiment of a knee joint 905 and femur 907 after the removal of the posterior of the intercondylar fossa. The notch 936 created by the removal of the posterior of the intercondylar fossa using the guide surface 952 is shown. In the depicted embodiment, the surface 937 of the notch 936 aligns with the guide surface 952 because the surgeon used the guide surface 952 when removing the posterior of the intercondylar fossa form the femur 907.

Figure 12:
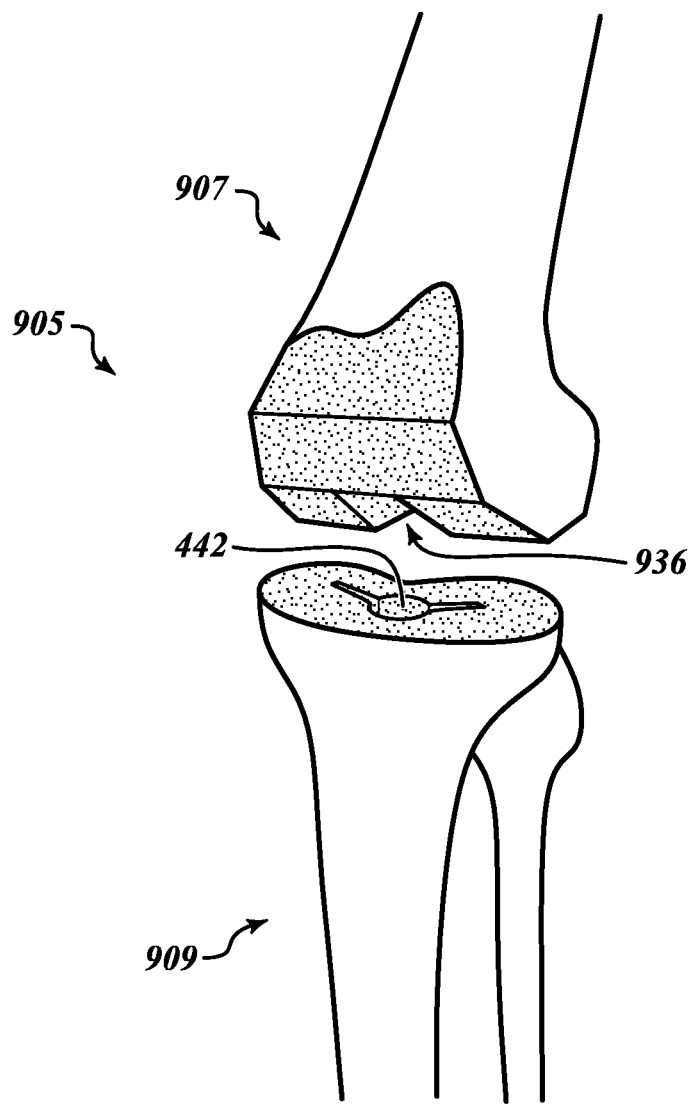
FIG. 12 depicts sectioned knee bones according to one or more embodiments disclosed herein.

FIG. 12 shows the knee joint 905, after a successful resection of the femur 907 and the tibia 909 and creation of the notch 936 and mounting cavity 442 in a knee replacement performed using the posterior cruciate ligament substituting/sacrificing technique. As shown, the femur 907 and the tibia 909 are prepared to accept a femoral component and tibia component.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A device for use in joint replacement surgery, the device comprising:
   a patient-specific jig having a body having a shape corresponding to three dimensional data of first and second resected planar surfaces of a bone of a patient according to a preoperative plan, the first resected planar surface of the bone having a first size and shape, the second resected planar surface having a third size and shape;
   the body including first and second bone facing planar surfaces, the first bone facing planar surface configured with a second size and shape that matches the first size and shape of the first resected planar surface of the bone of the patient according to the three dimensional data and the second bone facing planar surface configured with a fourth size and shape that matches the third side and shape of the second resected planar surface of the bone of the patient according to the three dimensional data;
   an outermost perimeter of the body surrounding the first and second bone facing planar surfaces and sized and shaped to nestingly mate with a non-resected perimeter of the resected planar surface of the bone of the patient in a single position according to the three dimensional data; and
   a plurality of individual alignment members extending from the body outward from the outermost perimeter, the plurality of alignment members including a respective alignment surface configured to nestingly mate in a single position with a respective portion of non-resected bone adjacent the first resected planar surface according to the three dimensional data of the bone structure of the patient.

2. The device for use in joint replacement surgery of claim 1, further comprising:
   guide holes passing through the body, the guide holes having an opening at the first bone facing planar surface and positioned and shaped according to the preoperative plan and a final installation position of the prosthesis.

3. The device for use in joint replacement surgery of claim 2 wherein the guide holes include guide surfaces orientated according to the preoperative plan and a final installation position of the prosthesis.

4. The device for use in joint replacement surgery of claim 1, further comprising:
   the first bone facing planar surface having a first edge and the second bone facing surface having a second edge, the first bone facing planar surface and second bone facing surface having different orientations and meeting at the first and second edges.

5. The device for use in joint replacement surgery of claim 1, further comprising:
   the plurality of alignment members extending from the outermost perimeter of the body, each of the plurality of alignment members configured to align with a respective one of a plurality of points of bone adjacent the resected planar surface according to the three dimensional data of the bone structure of the patient.

6. The device for use in joint replacement surgery of claim 1 wherein the body is configured to be positioned against a resected planar surface of a femur.

7. The device for use in joint replacement surgery of claim 1 wherein the body is configured to be positioned against a resected planar surface of a tibia.

8. The device for use in joint replacement surgery of claim 1 wherein the body is configured to be positioned against a resected planar surface of a patella.

9. The device for use in joint replacement surgery of claim 6 wherein the body includes a guide surface adjacent the posterior of an intercondylar fossa of the three dimensional data of the bone structure of the patient, the guide surface orientated to guide removal of a portion of the intercondylar fossa of the patient according to the preoperative plan.

10. A method of fabricating a jig for use in joint replacement surgery, the method comprising:
    using a computer processor to generate a bone surface image from three dimensional image data from the bone structure of a patient, the three dimensional image data being compiled from a scan of the bone structure of the patient;
    using a computer processor to generate a bone resection image based on a final installation position of a prosthesis relative to the three dimensional image data from the bone structure of a patient, the bone resection image including a perimeter of a first resection surface of the bone surface image;
    using a computer processor to generate a patient specific resection jig image superimposed proximate the bone resection image, the patient specific resection jig image depicting a device according to claim 1;
    using a computer processor to generate machine control data from the patient specific resection jig image such that the machine control data is capable of use in forming the device of claim 1, wherein the device of claim 1 is formed in the configuration of the jig image; and
    fabricating the device of claim 1 with an automated machine instructed by the machine control data such that the jig is capable of demonstrating a location of a resection on a resected bone being in a proper location as indicated in the resection image when each of the first and second planar surfaces, the outermost perimeter, and the plurality alignment members nestingly mate with the resected bone, such that the prosthesis will nestingly mate with the bone structure of the patient when the prosthesis is implanted.

11. The method for use in joint replacement surgery of claim 10, further comprising:
    generating a prosthesis image in an installation position superimposed on the bone surface image before the generating the bone resection image.

12. The method for use in joint replacement surgery of claim 10 wherein generating a bone resection image includes generating a bone surface image of at least a portion of a femur.

13. The method for use in joint replacement surgery of claim 10 wherein generating a bone resection image includes generating a bone surface image of at least a portion of a tibia.

14. The method for use in joint replacement surgery of claim 12 wherein generating a bone resection image includes generating a bone surface image of at least a portion of a tibia.

15. The method for use in joint replacement surgery of claim 14 wherein generating a bone resection image includes generating a bone surface image of at least a portion of a patella.

* * * * *